(12) United States Patent
Cox

(10) Patent No.: US 7,331,987 B1
(45) Date of Patent: Feb. 19, 2008

(54) INTRAVASCULAR STENT AND METHOD OF USE

(75) Inventor: Daniel L. Cox, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 586 days.

(21) Appl. No.: 10/222,731

(22) Filed: Aug. 16, 2002

(51) Int. Cl.
*A61F 2/82* (2006.01)
(52) U.S. Cl. .................................................. 623/1.16
(58) Field of Classification Search ............... 623/1.15, 623/1.16, 1.17, 1.2
See application file for complete search history.

(56) References Cited

U.S. PATENT DOCUMENTS

| | | | |
|---|---|---|---|
| 5,514,154 A * | 5/1996 | Lau et al. ................... | 623/1.15 |
| 5,755,781 A * | 5/1998 | Jayaraman .................. | 623/1.16 |
| 5,924,997 A | 7/1999 | Campbell | |
| 6,245,026 B1 | 6/2001 | Campbell et al. | |
| 6,273,910 B1 | 8/2001 | Limon | |
| 6,450,971 B1 | 9/2002 | Andrus et al. | |
| 6,451,044 B1 | 9/2002 | Naghavi et al. | |
| 6,875,227 B2 * | 4/2005 | Yoon ......................... | 623/1.16 |
| 2001/0047138 A1 | 11/2001 | Kokate et al. | |
| 2002/0009535 A1 | 1/2002 | Michal et al. | |
| 2002/0062147 A1 | 5/2002 | Yang | |
| 2002/0077564 A1 | 6/2002 | Campbell et al. | |
| 2002/0082515 A1 | 6/2002 | Campbell et al. | |
| 2002/0091436 A1 | 7/2002 | Phelps et al. | |
| 2002/0107561 A1 | 8/2002 | Pinheiro | |

FOREIGN PATENT DOCUMENTS

WO          01/89417        * 11/2001

OTHER PUBLICATIONS

Garasic, Joseph M., M.D., et al., *Stent and Artery Geometry Determine Intimal Thickening Independent of Arterial Injury*, Circulation, Feb. 22, 2000, pp. 812-818.
U.S. Appl. No. 10/034,208, filed Dec. 28, 2001 to Limon.
U.S. Appl. No. 10/280,632, filed Oct. 25, 2002 to Cox.

* cited by examiner

*Primary Examiner*—Michael Thaler
(74) *Attorney, Agent, or Firm*—Fulwider Patton LLP

(57) ABSTRACT

An expandable stent is implanted in a body lumen, such as a coronary artery, peripheral artery, or other body lumen for treating an area of vulnerable plaque. The invention provides for an intravascular stent having a plurality of cylindrical rings connected by straight links. Alternatively, the cylindrical rings of the distal section and the cylindrical rings of the proximal section are connected directly to adjacent cylindrical rings. The stent has adequate vessel wall coverage and radial strength sufficient to hold open an artery or other body lumen. A central section is positioned between distal and proximal sections and is aligned with the area of vulnerable plaque to enhance growth of cells over the fibrous cap of the vulnerable plaque to reinforce the area and reduce the likelihood of rupture.

26 Claims, 11 Drawing Sheets

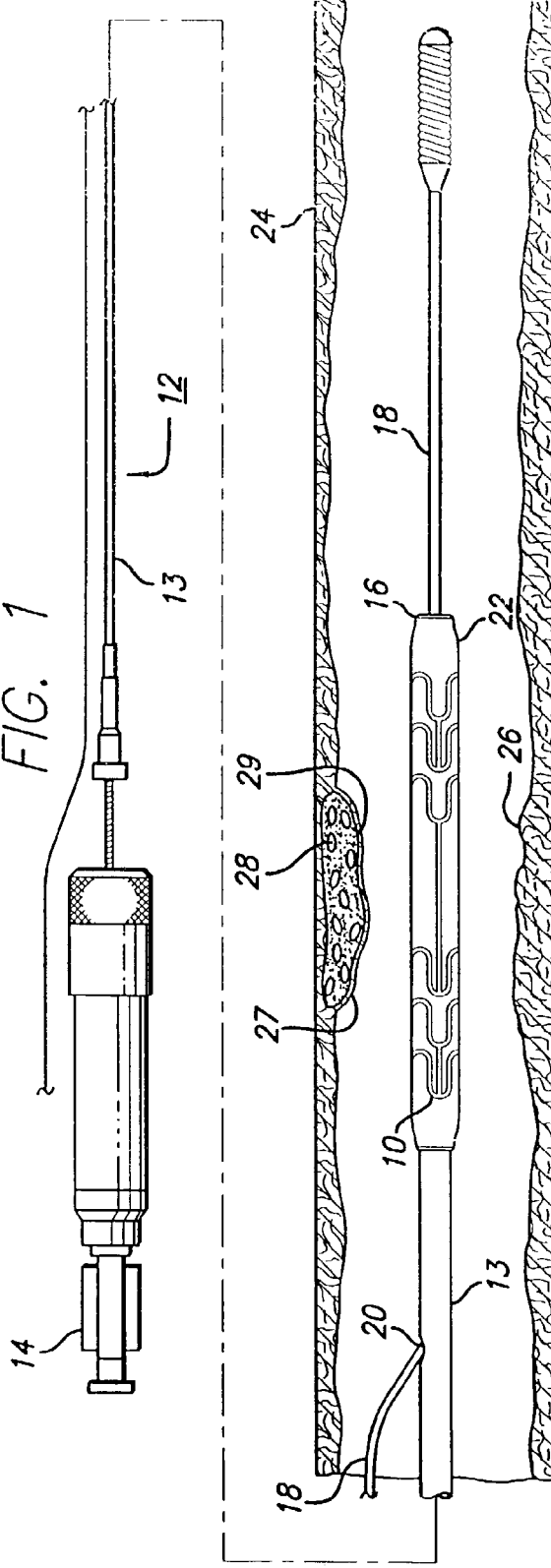
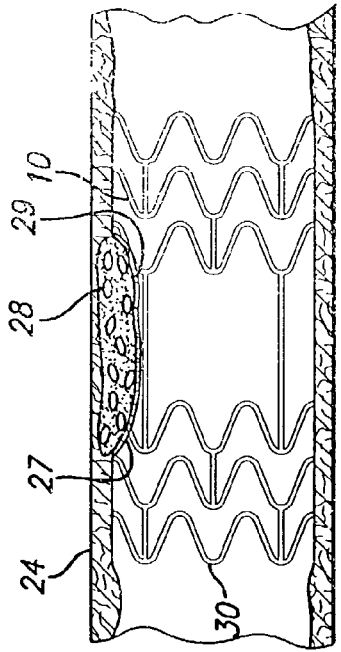
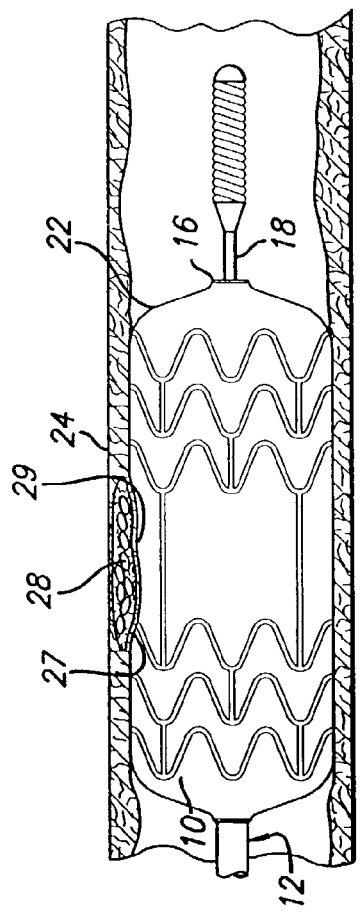
FIG. 1
FIG. 2
FIG. 3

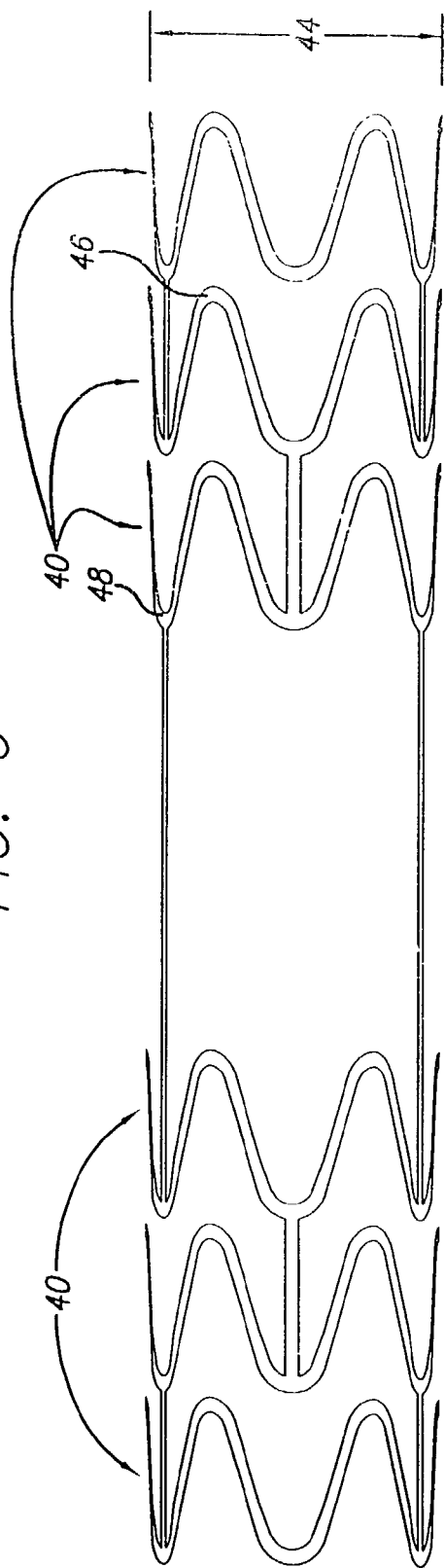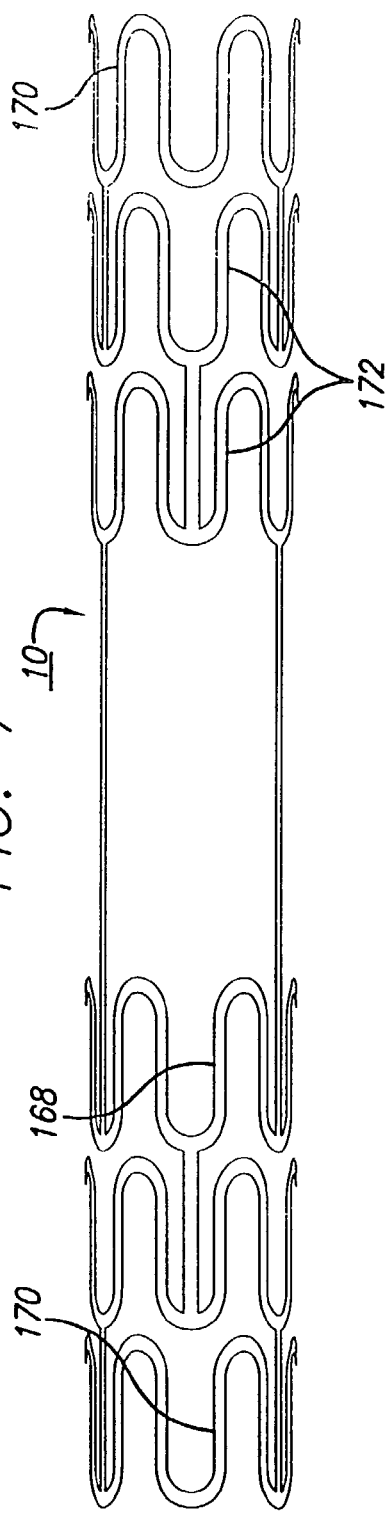
FIG. 6
FIG. 7

INTRAVASCULAR STENT AND METHOD OF USE

BACKGROUND OF THE INVENTION

This invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels.

Stents are generally tubular-shaped devices which function to hold open a segment of a blood vessel or other body lumen such as a coronary artery. They also are suitable for use to support and hold back a dissected arterial lining that can occlude the fluid passageway. At present, there are numerous commercial stents being marketed throughout the world. While some of these stents are flexible and have the appropriate radial rigidity needed to hold open a vessel or artery, there typically is a tradeoff between flexibility and radial strength.

Further, some coronary arteries may develop vulnerable plaque which may require treatment through stenting. Examples of stents which are configured to treat and repair vulnerable plaque can be found in utility application Ser. No. 10/034,208 filed Dec. 28, 2001, entitled "INTRAVASCULAR STENT AND METHOD OF USE," which is co-owned and co-assigned to Advanced Cardiovascular Systems, Inc., Santa Clara, Calif., the entire contents of which are incorporated herein by reference. What has been needed and heretofore unavailable is a stent that selectively reduces cell growth in one area, but enhances cell growth in other areas too, for example, cover the thin fibrous cap covering vulnerable plaque. The present invention satisfies these needs. The stent of the present invention has sufficient radial rigidity so that it can hold open an artery or other blood vessel, provide adequate vessel wall coverage, and enhance endothelial cell growth to reinforce the fibrous cover over any vulnerable plaque.

SUMMARY OF THE INVENTION

The present invention is directed to an intravascular stent which is flexible along its longitudinal axis to facilitate delivery through tortuous body lumens, but which is stiff and stable enough radially in its expanded condition to maintain the patency of a body lumen such as an artery when the stent is implanted therein. The novel stent pattern of the invention is particularly well suited for treating and repairing vulnerable plaque located in, for example, the coronary arteries.

The stent of the present invention generally includes a plurality of cylindrical rings that are interconnected to form a distal section and a proximal section, with a central section therebetween. The stent typically is mounted on a balloon catheter if it is balloon expandable or mounted on a catheter without a balloon if it is self expanding.

In one embodiment of the invention, the stent has a distal and proximal section formed of rings or cylindrical elements and links. The rings and links are configured so that the air to metal ratio is less than 90% (i.e., the metallic surface area is less than 10%) and preferably less than about 80% thus providing good scaffolding and providing a more cylindrical lumen. A central section is formed of stent struts that join the distal and proximal sections together. The central section strut pattern is less dense than the rings and links pattern of the distal and proximal sections. This central section scaffolds less, making the lumen less cylindrical. In use, the central section is aligned with an area of vulnerable plaque so that as smooth muscle cell growth occurs after the stent is implanted, in an attempt to form a cylindrical lumen, the central section strut pattern promotes cell growth over the struts and hence over the fibrous cap of the vulnerable plaque. This cell layer acts to protect the vulnerable plaque from rupturing and possibly embolizing in the artery. Comparatively, the rings and links pattern of the distal and proximal sections inhibit smooth muscle cell growth thereby maintaining a patent lumen for blood flow. Thus, the present invention stent promotes cell growth where needed, to cover and reinforce the vulnerable plaque area, and inhibits cell growth in other areas so that the lumen (artery) remains patent for maximum blood flow.

The central section of the stent includes struts that connect the distal and proximal section together. The central section struts can take different configurations and still function to hold open the vessel and promote cell growth. In one embodiment of the invention, the struts are substantially straight and extend substantially longitudinally between a valley of the distal section of the stent to a valley of the proximal section of the stent. In other embodiments of the invention, the struts may include an undulating member or a series of undulating members. The length of the central section struts for all of the embodiments will depend on the length of the vulnerable plaque area to be repaired. If the plaque area is 6 to 8 mm in length, then the struts of the central section would be of a similar length or slightly longer. Typically, a coronary stent might be 18 mm long, therefore in one example, the central section struts would be 8 mm long and the distal and proximal sections each would be about 5 mm.

The cylindrical rings and links can have various configurations. In one embodiment, each of the cylindrical rings making up the stent have a proximal end and a distal end and a cylindrical plane defined by a cylindrical outer wall surface that extends circumferentially between the proximal end and the distal end of the cylindrical ring. Each of the cylindrical rings of the proximal and distal sections includes an undulating pattern of U-shaped portions having peaks, valleys and substantially straight portions therebetween. The peaks of one ring are substantially circumferentially aligned with the peaks of an adjacent ring. At least one substantially straight link attaches one cylindrical ring to an adjacent cylindrical ring so that each substantially straight link connects one of the valleys on one ring to a valley on the adjacent ring. The links are positioned substantially within the cylindrical plane of the outer wall surface of the cylindrical rings. The design of the links and their placement provides for uniform scaffolding and a high degree of vessel wall coverage at the proximal and distal sections. Further, the cylindrical rings are configured to provide flexibility to the stent in that the portions of the rings can flex or bend and tip outwardly as the stent is delivered through a tortuous vessel.

While the cylindrical rings and links generally are not separate structures, they have been conveniently referred to as rings and links for ease of identification. Further, the cylindrical rings can be thought of as comprising a series of U-shaped structures in a repeating pattern. Again, while the cylindrical rings are not divided up or segmented into U's, the pattern of the cylindrical rings resemble such configuration. The U's promote flexibility in the stent primarily by flexing and by tipping radially outwardly as the stent is delivered through a tortuous vessel.

The number and location of links that interconnect adjacent cylindrical rings can be varied as the application requires. The links typically do not expand when the cylindrical rings of the stent expand radially outwardly. The links continue to provide a scaffolding function to assist in holding open the artery.

In a further embodiment of the invention, each of the cylindrical rings of the proximal and distal sections includes an undulating pattern of U-shaped portions having peaks, valleys and substantially straight portions therebetween. The peaks of one ring are circumferentially offset from the peaks of an adjacent ring. The peaks of one cylindrical ring may be attached directly to the valleys of an adjacent ring, thereby having no separate links between adjacent cylindrical rings. The struts associated with cylindrical rings of this configuration may include many forms. For example, in one embodiment of the invention, each of the struts includes a series of undulating members. In another embodiment of the invention, the struts are substantially straight and positioned non-longitudinally (angled) such that a distal end of the strut attaches to a peak of the distal section. The proximal end of the strut attaches to the proximal section at a valley which is adjacent the valley that is substantially circumferentially aligned with the peak of the distal section to which the distal end of the strut is attached. The struts of the first and second aspect of the invention may be positioned asymmetrically about the circumference of the stent to maximize flexibility of the stent and to promote fibrous cap growth in a desired area. In a further embodiment of the invention, the struts include an undulating pattern of U-shaped portions similar to the cylindrical rings of the proximal and distal sections, except that the substantially straight portions of the strut are longer than the substantially straight portions of the cylindrical rings of the proximal and distal sections.

The cylindrical rings of the stent are plastically deformed when expanded when the stent is made from a metal that is balloon expandable. Typically, the balloon expandable stent is made from a stainless steel alloy or similar material. Similarly, the cylindrical rings of the stent expand radially outwardly when the stent is formed from a superelastic alloy, such as nickel titanium (NiTi). In the case of superelastic alloys, the stent expands upon application of a temperature change or when a stress is relieved, as in the case of a pseudoelastic phase change.

In one embodiment, one or more sections of the stent are covered with a material such as PTFE or ePTFE. For example, the central section can be partially or completely covered with a sheath of material so that when the stent is implanted, the sheath aligns with and provides covering support for the vulnerable plaque.

The stent may be formed from a tube by laser cutting the pattern of cylindrical rings, links, and central section struts in the tube. The stent also may be formed by laser cutting a flat metal sheet in the pattern of the struts, cylindrical rings, and links, and then rolling the pattern into the shape of the tubular stent and providing a longitudinal weld to form the stent.

It is to be understood that the present invention is not limited by the embodiments described herein. Other features and advantages of the present invention will become more apparent from the following detailed description of the invention, when taken in conjunction with the accompanying exemplary drawings, which illustrate by way of example the features of the invention.

BRIEF DESCRIPTION OF THE DRAWINGS

FIG. 1 is an elevational view, partially in section, of a stent embodying features of the invention and which is mounted on a rapid-exchange delivery catheter and positioned within an artery.

FIG. 2 is an elevational view, partially in section, similar to that shown in FIG. 1 wherein the stent is expanded within the artery, so that the stent embeds within the arterial wall.

FIG. 3 is an elevational view, partially in section, showing the expanded stent implanted within the artery after withdrawal of the rapid-exchange delivery catheter.

FIG. 6 is a side view of the stent of FIG. 5A in an expanded condition.

FIG. 7 is a side view of the stent depicting cylindrical rings at the end of the stent having a thicker cross-section than the rings at the center of the stent.

DETAILED DESCRIPTION OF THE PREFERRED EMBODIMENTS

Figure 4:
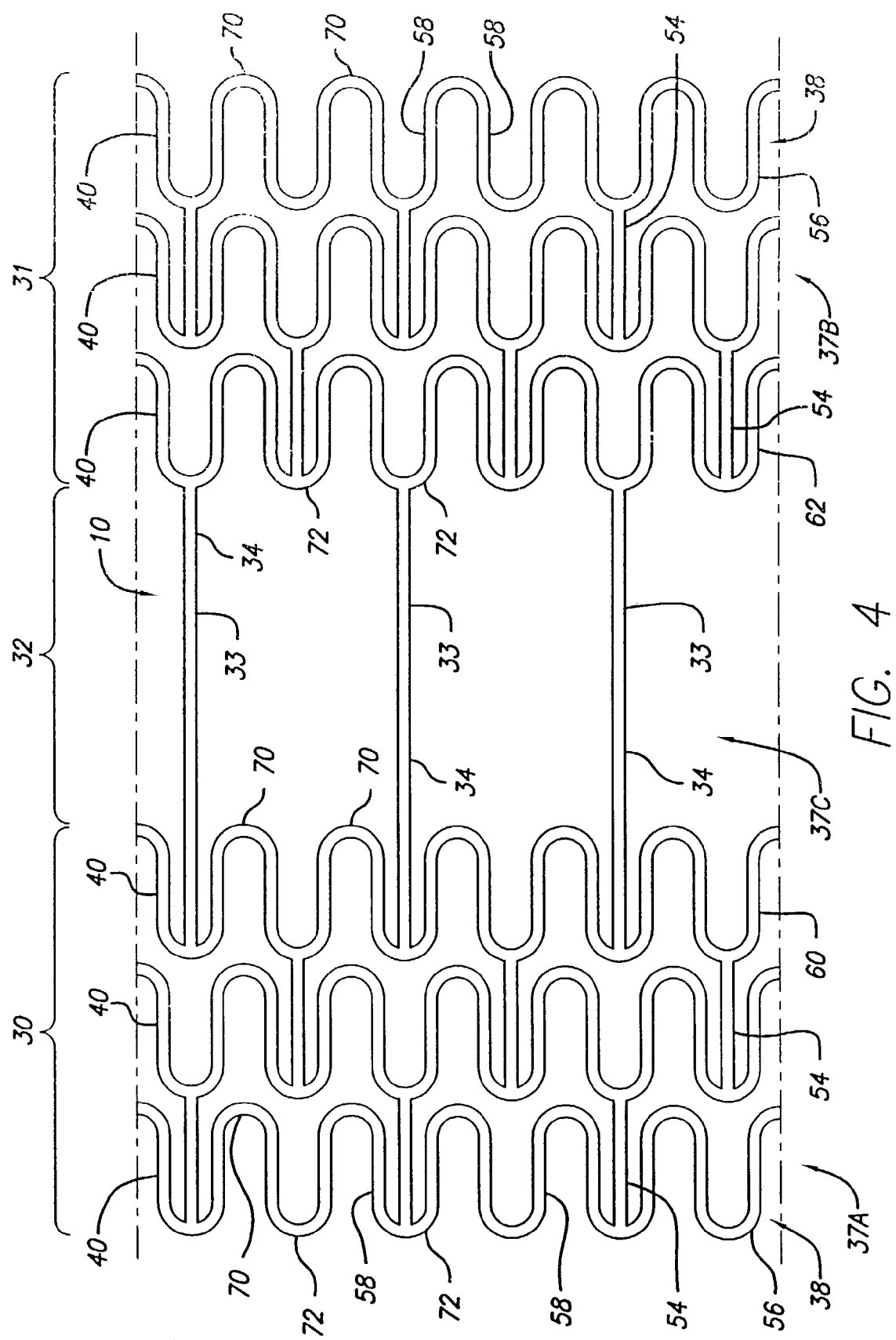
FIG. 4 is a plan view of a flattened stent of the invention which illustrates the pattern of the stent shown in FIGS. 1-3.

The present invention stent improves on existing stents by providing a uniquely designed pattern. The stent of the present invention provides radial rigidity and a high degree of scaffolding of a vessel wall at the stent ends and less scaffolding in the central section to intentionally promote smooth muscle cell growth over the central section. The design of the links and cylindrical rings of the distal and proximal sections provides for uniform scaffolding and a high degree of vessel wall coverage while the struts of the central section provide comparatively minimal vessel wall coverage.

Turning to the drawings, FIG. 1 depicts the present invention stent 10 mounted on a catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

The catheter assembly 12, as depicted in FIG. 1, is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque 26 that has been previously treated by an angioplasty or other repair procedure. The stent 10 of the present invention is used to repair a diseased or damaged arterial wall which may include the plaque 26 as shown in FIG. 1, or vulnerable plaque 27 which is commonly found in the coronary arteries, peripheral arteries and other vessels. Vulnerable plaque consists of a thrombogenic lipid 28 that is covered by a thin fibrous cap 29. The stent of the invention is configured to repair the vessel having both plaque and vulnerable plaque.

In a typical procedure to implant the stent 10, the guide wire 18 is advanced through the patient's vascular system by well known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire is typically left in the lumen for post-dilatation procedures, if any, and subsequently is withdrawn from the patient's vascular system. As depicted in FIG. 2, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 serves to hold open the artery after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with smooth muscle cell growth which further minimizes blood flow interference. The undulating portion of the stent provides good tacking characteristics to prevent stent movement within the artery.

In keeping with the present invention, FIGS. 4-7 depict the stent 10 in various configurations. Turning to FIG. 4, stent 10 is shown in a flattened condition so that the pattern can be clearly viewed, even though the stent is never in this form unless it is formed from a flat sheet. The stent is typically formed from a tubular member, however, it can be formed from a flat sheet such as shown in FIG. 4 and rolled into a cylindrical configuration.

Figure 8:
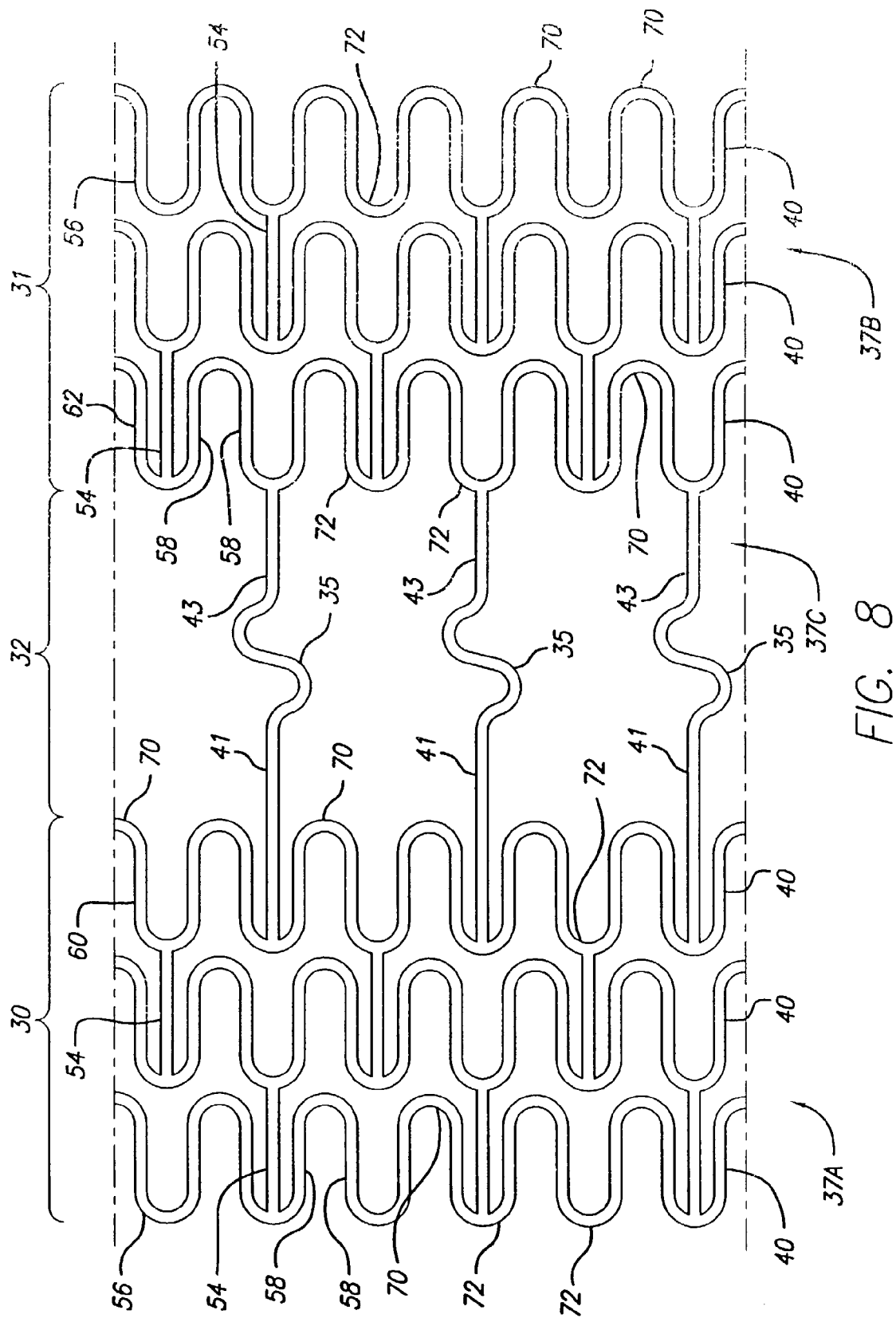
FIG. 8 is a plan view of a flattened stent which illustrates the stent pattern of another embodiment of the invention.
Figure 9:
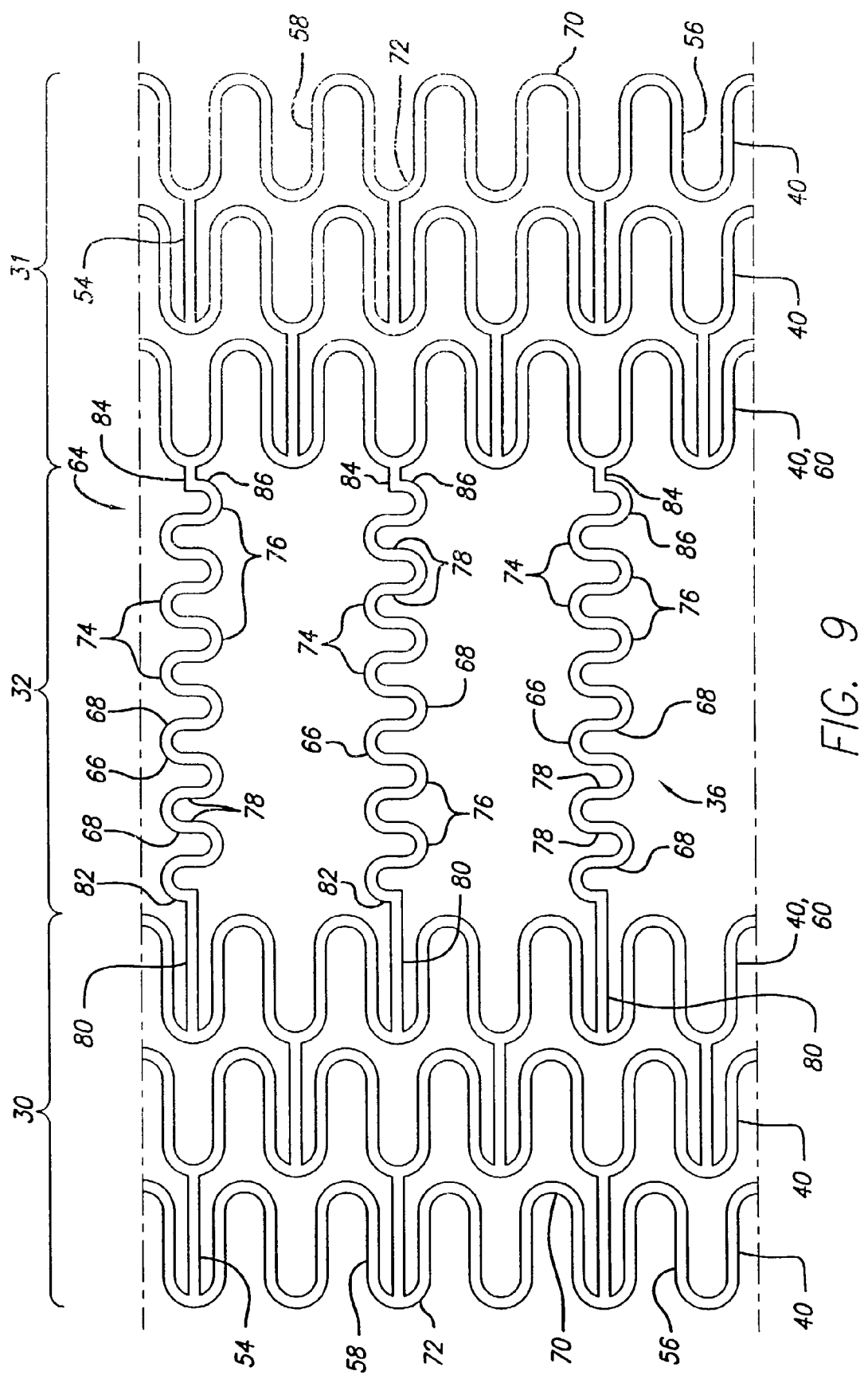
FIG. 9 is a plan view of a flattened stent which illustrates the stent pattern of another embodiment of the invention.

The stent of the present invention is particularly useful in treating vulnerable plaque 27 which generally comprises a thrombogenic lipid 28 that has accumulated and is covered by a thin fibrous cap 29. As shown in FIGS. 4-7, the stent is designed to have three sections, a distal section 30, a proximal section 31 and a central section 32 positioned between the distal and proximal sections with each section being substantially longitudinally aligned along a common longitudinal axis. The distal section and the proximal section may each include a plurality of substantially cylindrical rings 40 which are connected by one or more links 54, both of which will be further described herein. With respect to the central section 32, it is designed to be aligned with the vulnerable plaque in the area of the fibrous cap so that after the stent is implanted, smooth muscle cells will accumulate and readily grow over the central section thereby reinforcing the fibrous cap and preventing rupture, and thence emboli in the form of the released thrombogenic lipid. The central section 32 may include a plurality of struts 33 which are depicted as being substantially straight 34, however, the struts can have an undulating member 35 positioned between a first substantially straight portion 41 and a second substantially straight portion 43 as depicted in FIG. 8 or a series of undulating members 36 as depicted in FIG. 9. The struts form the connection between the distal section 30 and the proximal section 31.

It has been shown through empirical data that increasing the number of struts per cross-section provides an associated drop in neointimal thickening after a short period of time. In other words, the distal section 30 and the proximal section 32 have a higher density of struts in the form of cylindrical rings and links than does the central section 32 having struts 33. Based on the empirical data, the struts 33 will promote development of neointimal thickness along the struts which are aligned with the fibrous cap, thereby providing a thickening of cell growth over the fibrous cap and reinforcing the area in order to prevent rupture of the thrombogenic lipid into an artery or other vessel.

The stent 10 of the present invention also can be described has having a first strut pattern 37A and a second strut pattern 37B in the distal section 30 and the proximal section 31, respectively. A third strut pattern 37C is formed in the central section and includes struts 33 which can either be straight 34 or undulating struts 35, 36. The straight struts and the undulating struts form the connection between the first strut pattern in the distal section 30 and the second strut pattern in the proximal section 31.

With respect to the structure of the cylindrical rings and links, virtually any pattern is acceptable as long as the pattern of struts are more dense than the strut pattern in the central section 32. Typically, the rings are in the form of a generally undulating pattern 38 that can easily expand radially outwardly or compress radially inwardly. Thus, as described immediately below, currently preferred examples of cylindrical rings 40 and links 54 are described, however, other patterns are envisioned that would perform equally as well in inhibiting growth of smooth muscle cells at the stent proximal and distal ends and more specifically in the distal section 30 and the proximal section 31.

Figure 5:
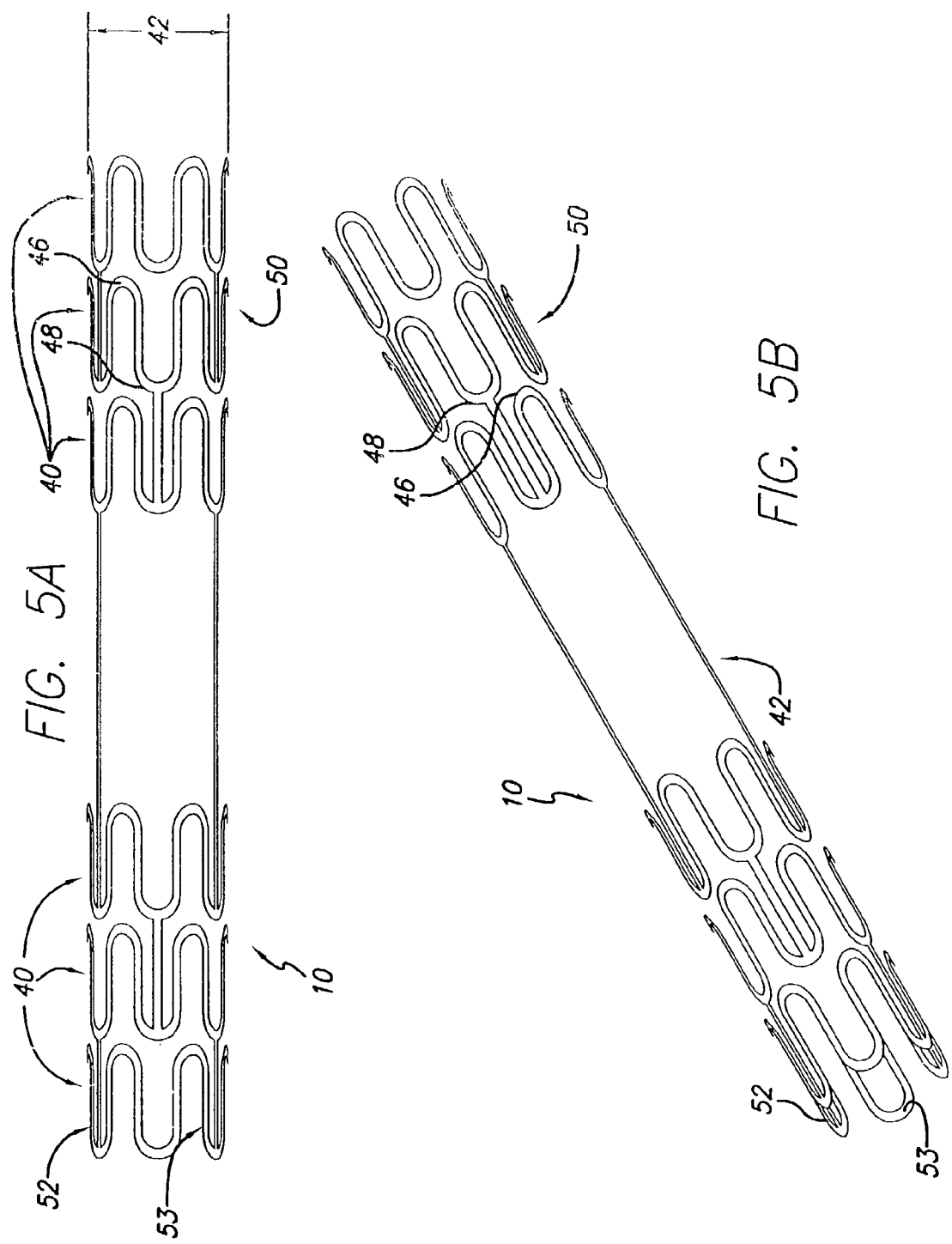
FIG. 5A is a side view of a stent embodying features of the invention in an unexpanded state.
FIG. 5B is a perspective view of the stent of FIG. 5A depicting the cylindrical wall defined by each cylindrical ring.

As shown in FIGS. 4-7, stent 10 is made up of a plurality of cylindrical rings 40 which extend circumferentially around the stent when it is in a tubular form (see FIGS. 5A and 5B). The stent has a delivery diameter 42 as shown in FIGS. 5A and 5B, and an implanted diameter 44 as shown in FIG. 6. Each cylindrical ring 40 has a cylindrical ring proximal end 46 and a cylindrical ring distal end 48.

Typically, since the stent is laser cut from a solid tube there are no discreet parts such as the described cylindrical rings. However, it is beneficial for identification and reference to various parts to refer to the cylindrical rings and the following parts of the stent.

Each cylindrical ring 40 defines a substantially cylindrical plane 50 which is a plane defined by the proximal and distal ends 46, 48 and the circumferential extent as the cylindrical ring travels around the cylinder. Each cylindrical ring includes a substantially cylindrical outer wall surface 52 which defines the outermost surface of the stent, and a substantially cylindrical inner wall surface 53 which defines the innermost surface of the stent. The cylindrical plane 50 follows the cylindrical outer wall surface. In keeping with the invention, the link 54 is positioned within the cylindrical plane 50. The links connect one cylindrical ring to an adjacent cylindrical ring.

The cylindrical rings 40 can be nested such that adjacent rings slightly overlap in the longitudinal direction so that one ring is slightly nested within the next ring and so on. The degree of nesting is dictated primarily by the length of each cylindrical ring, the number of undulations in the rings, the thickness of the struts that make up the rings, and the radius of curvature, all in conjunction with the crimped or delivery diameter of the stent. If the rings are substantially nested one within the other, it may be difficult to crimp the stent to an appropriate delivery diameter without the various struts overlapping. It is also contemplated that the rings are slightly nested even after the stent is expanded, which enhances vessel wall coverage. In some circumstances, it may not be desirable to nest one ring within the other, which is also contemplated by the invention.

Referring to FIGS. 4-7, the stent 10 can be described more particularly as having a plurality of peaks 70 and valleys 72. Although the stent is not divided into separate elements, for ease of discussion references to peaks and valleys is appropriate. The number of peaks and valleys, sometimes referred to as crowns, can vary in number for each ring depending upon the application. Thus, for example, if the stent is to be implanted in a coronary artery, a lesser number of peaks and valleys (or crowns) are required than if the stent is implanted in a peripheral artery, which has a larger diameter than a coronary artery.

More particularly, with reference to FIGS. 4, 8 and 9, some currently preferred stent patterns which are useful in treating vulnerable plaque 27 are depicted in a flattened condition so that the patterns can be clearly viewed. With continued reference to FIG. 4, each of the rings 40 includes an undulating pattern, such as a series of U-shaped portions 56 having peaks 70 and valleys 72 with substantially straight portions 58 which are substantially parallel with the longitudinal axis of the stent extending between the peaks and valleys. As shown in FIGS. 4, 8 and 9, the peaks 70 of adjacent rings 40 are in phase, such that the peaks of adjacent rings are substantially circumferentially aligned. The links 54 connect adjacent rings between alternating valleys, or alternatively between alternating peaks (not shown), with the link pattern being circumferentially offset between adjacent rings. The links may be substantially straight and extend substantially parallel to the longitudinal axis of the stent. The struts 33 extend substantially parallel to the longitudinal axis of the stent such that a distal end of each strut is circumferentially aligned with a proximal end of the strut. In such manner, the struts connect alternating valleys of the proximal ring 60 of the distal section 30 of the stent to substantially circumferentially aligned alternating valleys of the distal ring 62 of the proximal section 31 of the stent. Alternatively, the struts may connect peaks from the distal section of the stent to substantially circumferentially aligned peaks of the proximal section of the stent.

Referring to FIG. 9, a stent 64, which is similar to stent 10 of FIG. 4, is depicted having struts 66 with undulating members 36. The undulating members 36 may include a series of U-shaped portions 68 having peaks 74 and valleys 76 with substantially straight portions 78 which are substantially perpendicular to the longitudinal axis of the stent extending between the peaks and valleys. The distal end of each of the struts 66 includes a first substantially straight arm 80 extending from the distal undulating member 82 of the strut to a valley 72 of the proximal ring 60 of the distal section 30 of the stent. Similarly, the proximal end of each of the struts 66 includes a second substantially straight arm 84 extending from the proximal undulating member 86 of the strut to a valley 72 of the distal ring 60 of the proximal section 31 of the stent. The lengths of the first arm 80 and the second arm 84 may vary. The first and second arms are sized in conjunction with the undulating members of the struts so that the struts are properly positioned in the central section 132 of stent 64.

Figure 10:
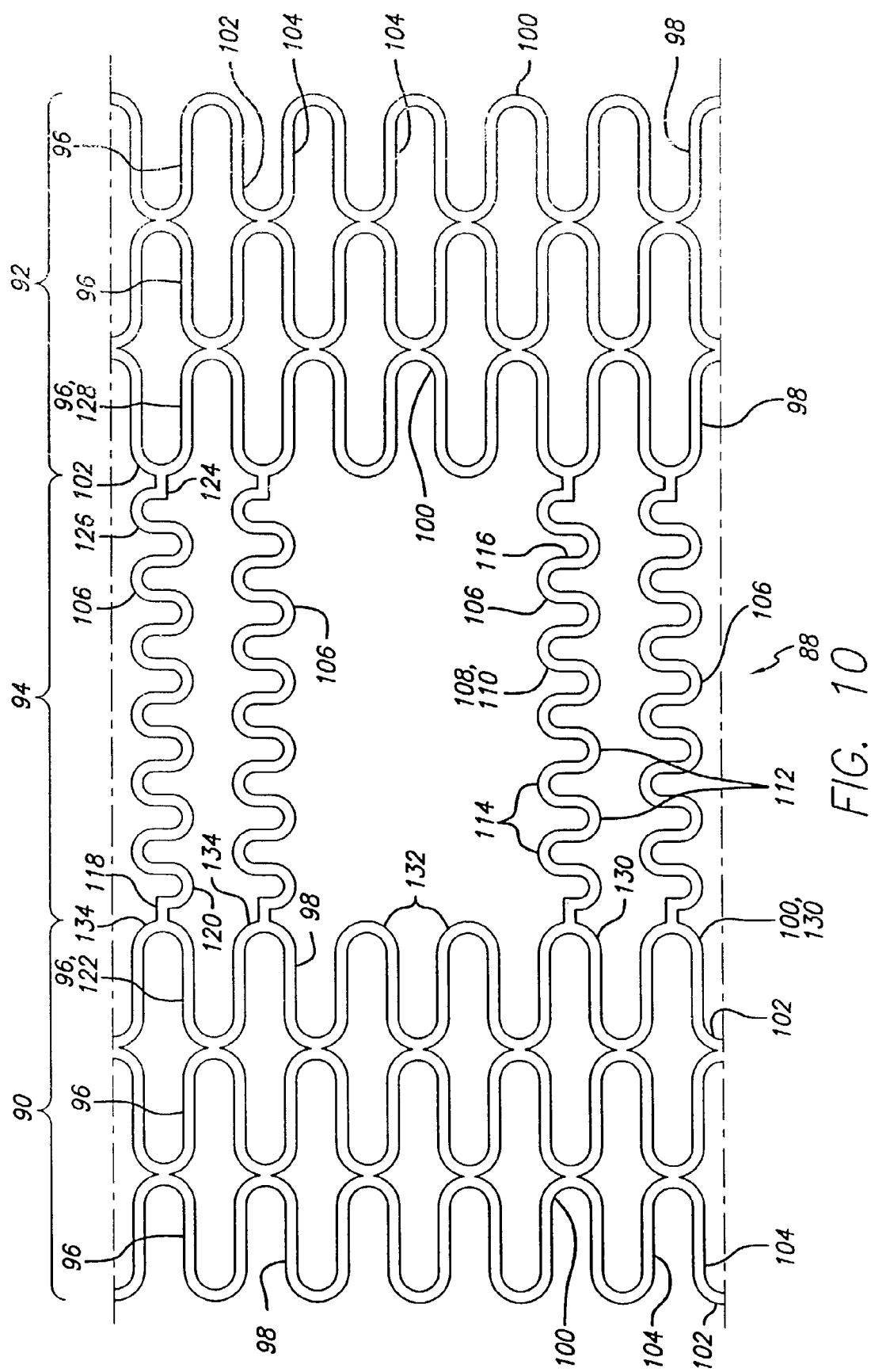
FIG. 10 is a plan view of a flattened stent which illustrates the stent pattern of another embodiment of the invention.
Figure 11:
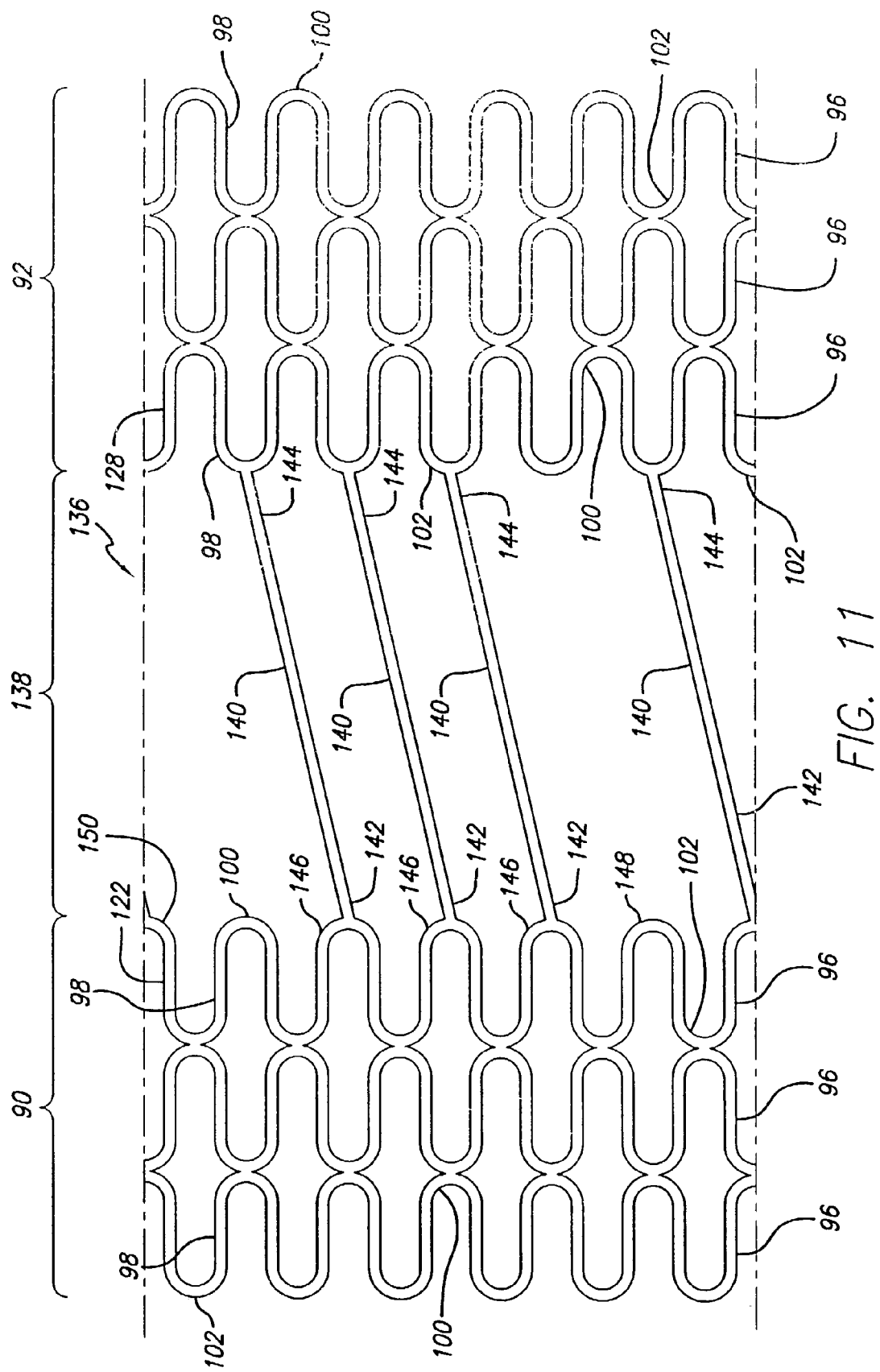
FIG. 11 is a plan view of a flattened stent which illustrates the stent pattern of another embodiment of the invention.
Figure 12:
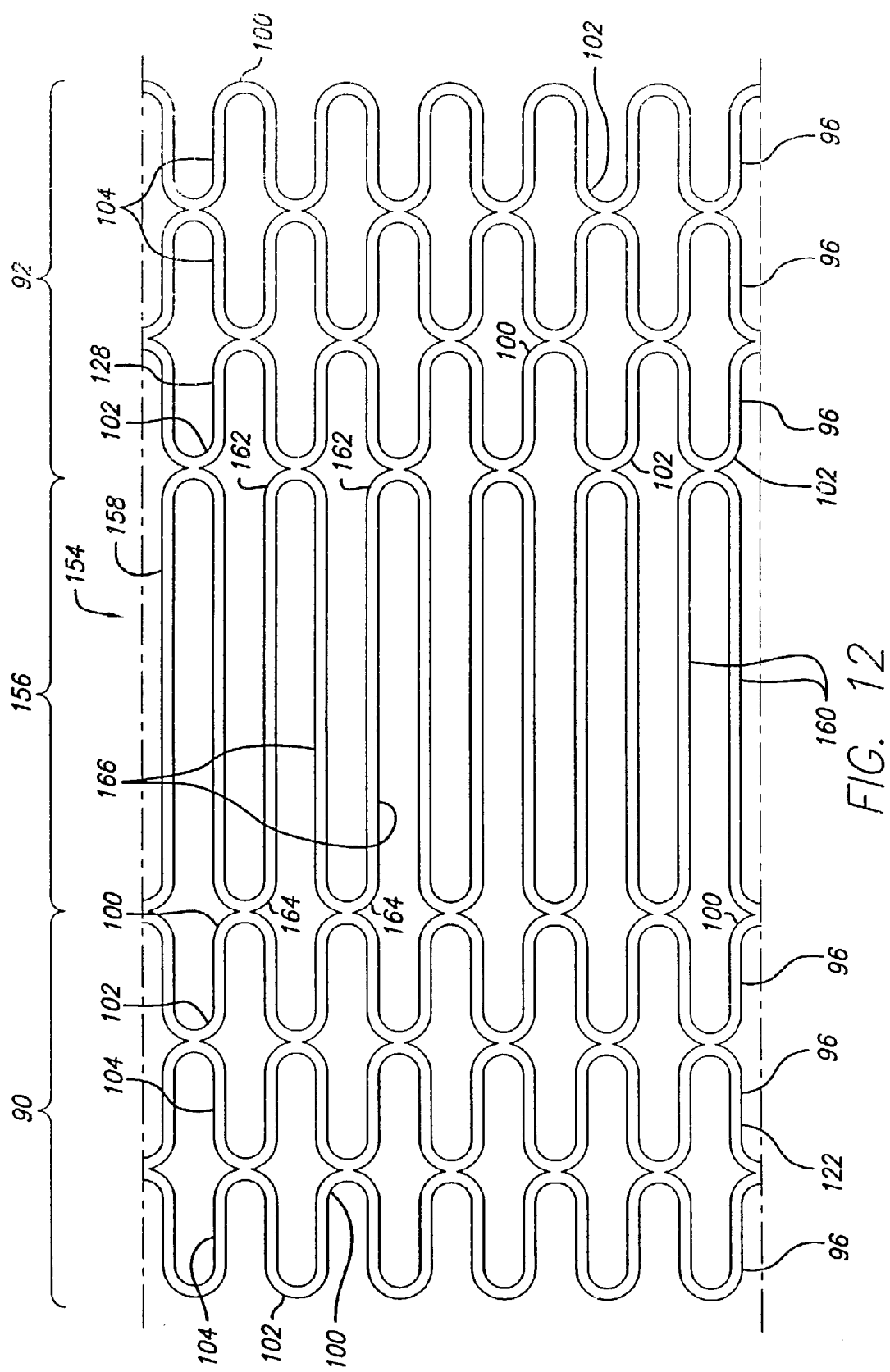
FIG. 12 is a plan view of a flattened stent which illustrates the stent pattern of another embodiment of the invention.

With reference to FIGS. 10-12, other embodiments of the invention include stent patterns which are similar to the stent patterns depicted in FIGS. 4, 8 and 9. More particularly, as depicted in FIG. 10, a stent 88 includes a distal section 90, a proximal section 92 and a central section 94 positioned between the distal and proximal sections with each section being substantially aligned along a common longitudinal axis. The distal section and the proximal section may each include a plurality of substantially cylindrical rings 96. Each of the rings 96 includes an undulating pattern, such as a series of U-shaped portions 98 having peaks 100 and valleys 102 with substantially straight portions 104 which are substantially parallel with the longitudinal axis of the stent extending between the peaks and valleys. As shown in FIG. 10, the peaks 100 of adjacent rings 96 are out of phase, such that the peaks of adjacent rings are circumferentially offset from each other. Moreover, the peaks of one cylindrical ring are substantially circumferentially aligned with the valleys on an adjacent cylindrical ring. The peaks of the distal ring of a pair of adjacent rings may be connected directly to the valleys of the proximal ring of the pair of adjacent rings. Some of the adjacent peaks and valleys do not need to be connected, thereby improving flexibility of the end portions.

With continued reference to FIG. 10, the central section 94 of the stent 88 may include a plurality of struts 106 which are similar to the struts 66 depicted in FIG. 9, having undulating members 108 which include a series of U-shaped portions 110. The U-shaped portions include peaks 112 and valleys 114 with substantially straight portions 116 which are substantially perpendicular to the longitudinal axis of the stent extending between the peaks and valleys. The distal end of each of the struts 106 includes a first substantially straight arm 118 extending from the distal undulating member 120 of the strut to the proximal ring 122 of the distal section 90 of the stent. The proximal end of each of the struts 106 includes a second substantially straight arm 124 extending from the proximal undulating member 126 of the strut to the distal ring 128 of the proximal section 92 of the stent. However, with the peaks 100 of the rings 96 positioned out of phase, the first arm 118 of each of the struts may connect to a peak 100 on the proximal ring 122 of the distal section 90 while the second arm 124 of each of the struts connects to a valley 102 on the distal ring 128 of the proximal section 92 of the stent. Alternatively, the first arm 118 of each of the struts may connect to a valley 102 on the proximal ring 122 of the distal section 90 while the second arm 124 of each of the struts connects to a peak 100 on the distal ring 128 of the proximal section 92 of the stent. Being positioned in such manner, the distal end of each strut is substantially circumferentially aligned with the proximal end of the strut. The struts may be positioned asymmetrically to maximize flexibility of the stent and to promote fibrous cap growth in a desired area. For example, FIG. 10 depicts struts 106 connected to a pair of adjacent peaks 130 on the proximal ring 122 of the distal section 90 of the stent, no strut connected to the next pair of adjacent peaks 132, and struts connected to the following pair of adjacent peaks 134.

Referring to FIG. 11, a further embodiment of the invention includes a stent 136 having rings 96 within a distal section 90 and within a proximal section 92 which are similar to the rings within the stent 88 of FIG. 10. As in FIG. 10, the rings include peaks 100 and valleys 102 with the peaks of adjacent rings being positioned out of phase, such that the peaks of one ring are circumferentially offset from the peaks of an adjacent ring. To create a rifling profile within the artery 24, a central section 138 of the stent 136 includes substantially straight struts 140 which are positioned non-longitudinally such that a distal end of each strut is circumferentially offset from a proximal end of the strut. More particularly, as depicted in FIG. 11, the distal end 142 of each of the struts 140 may be connected to a peak 100 on the proximal ring 122 of the distal section 90 of the stent. The proximal end 144 of each of the struts 140 may be connected to the distal ring 128 of the proximal section 92 at a valley 102 which is adjacent to the valley that is substantially circumferentially aligned with the peak to which the distal end 142 of the strut is connected. Furthermore, the struts 140 may be positioned asymmetrically about the circumference of the stent. For example, FIG. 11 depicts a series of three struts 140 with the distal ends 142 of each of the struts connected to corresponding adjacent peaks 146 on the proximal ring 122 of the distal section 90 of the stent. There is no strut 140 connected to the next adjacent peak 148 on the proximal ring 122 of the distal section 90, however, a strut is connected to the following peak 150 on the proximal ring of the distal section.

With reference to FIG. 12, another embodiment of the invention includes a stent 154 having a plurality of cylindrical rings 96 within a distal section 90 and within a proximal section 92 which are similar to the cylindrical rings within the stent 88 of FIG. 10 and the stent 136 of FIG. 11. As in FIGS. 10 and 11, the rings include peaks 100 and valleys 102 with the peaks of adjacent rings being positioned out of phase, such that the peaks of one ring are circumferentially offset from the peaks of an adjacent ring. A central section 156 of the stent 154 includes a substantially cylindrical ring 158 having an undulating pattern, such as a series of U-shaped portions 160. The U-shaped portions 160 include peaks 162 at a proximal end of the cylindrical ring 158 and valleys 164 at a distal end of the cylindrical ring 158 with substantially straight portions 166 which are substantially parallel with the longitudinal axis of the stent extending between the peaks and valleys. The straight portions 166 of the ring 158 of the central section 156 are longer than the straight portions 104 of the rings 96 of the distal section 90 and the proximal section 92. In one currently preferred embodiment, the number of valleys 164 at the distal end of the ring 158 of the central section 156 is equal to the number of peaks 100 within the proximal ring 122 of the distal section 90. Similarly, the number of peaks 162 at the proximal end of the ring 158 of the central section is equal to the number of valleys 102 within the distal ring 128 of the proximal section 92. The peaks 162 of the ring 158 of the central section 156 are out of phase with the peaks 100 of the distal section 90 and the peaks 100 of the proximal section 92. Each of the valleys 164 at the distal end of the ring 158 of the central section 156 may be directly connected to a corresponding peak 100 within the proximal ring 122 of the distal section 90, while each of the peaks 162 at the proximal end of the ring 158 of the central section may be directly connected to a corresponding valley 102 within the distal ring 128 of the proximal section 92.

In one aspect of the invention, the stent is formed so that the struts 168 (FIG. 7) have variable thickness along the stent length. As one example, it is contemplated that the struts 170 at the ends of the stent may be thicker than the struts 172 in the center of the stent for purposes of radiopacity and to counter balloon expansion. When the balloon first inflates, the balloon ends have a tendency to inflate at a faster rate than the balloon center, however, with thicker struts at the stent ends the balloon, and hence the stent, will expand more uniformly.

As described above, it is also contemplated that more or fewer links 54 will be positioned between adjacent cylindrical rings 40. The links will provide stability and assist in preventing stent foreshortening. The straight links allow the rings to be crimped or compressed more tightly at the stent ends, in comparison to undulating links, which aids in delivering the stent through tortuous arteries. Further, in comparison to undulating links, the straight links may provide more rigidity in a localized area, such as at the stent ends, such that it may be desirable to incorporate more straight links between the cylindrical rings at the stent ends, than in the center of the stent.

In one important aspect of the invention, after the stent 10 is implanted in a coronary artery, or other vessel, because of its novel design, the cylindrical rings 40 have the ability to flex radially as the vessel pulsates when blood pumps through it. The radial flexing of the stent reduces the likelihood that the stent will cause injury to the intima of a coronary artery, which also may have a tendency to reduce the likelihood of restenosis.

Any portion of the disclosed stents can be made from a metal alloy or from a polymer. For example, the cylindrical rings can be made from a metal alloy while the connecting links can be made from a metal alloy or a polymer. Typically, if the links are made from a polymer, the stent will be more longitudinally flexible than if the links were made from a metal alloy. Also, the central section struts can be made from either a metal alloy or a polymer.

Exemplary of the metallic material used in forming the cylindrical rings and links of the stent is stainless steel, titanium, nickel titanium, tantalum, gold, cobalt-chromium, platinum, palladium, and iradium. Other metals, metal alloys and polymers may also be used to form the present invention stent.

Exemplary of the biocompatible polymer material used in forming the central section struts, the rings, or the links includes the group of polymers consisting of polyurethanes, polyetherurethanes, polyesterurethanes, silicone, thermoplastic elastomer (C-flex), polyether-amide thermoplastic elastomer (Pebax), fluoroelastomers, fluorosilicone elastomer, styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile rubber, a family of elastomers composed of styrene, ethylene, propylene, aliphatic polycarbonate polyurethane, polymers augmented with antioxidants, polymers augmented with image enhancing materials, polymers having a proton (H+) core, polymers augmented with protons (H+), butadiene and isoprene (Kraton) and polyester thermoplastic elastomer (Hytrel), polyethylene, PLA, PGA, and PLGA.

Figure 13:
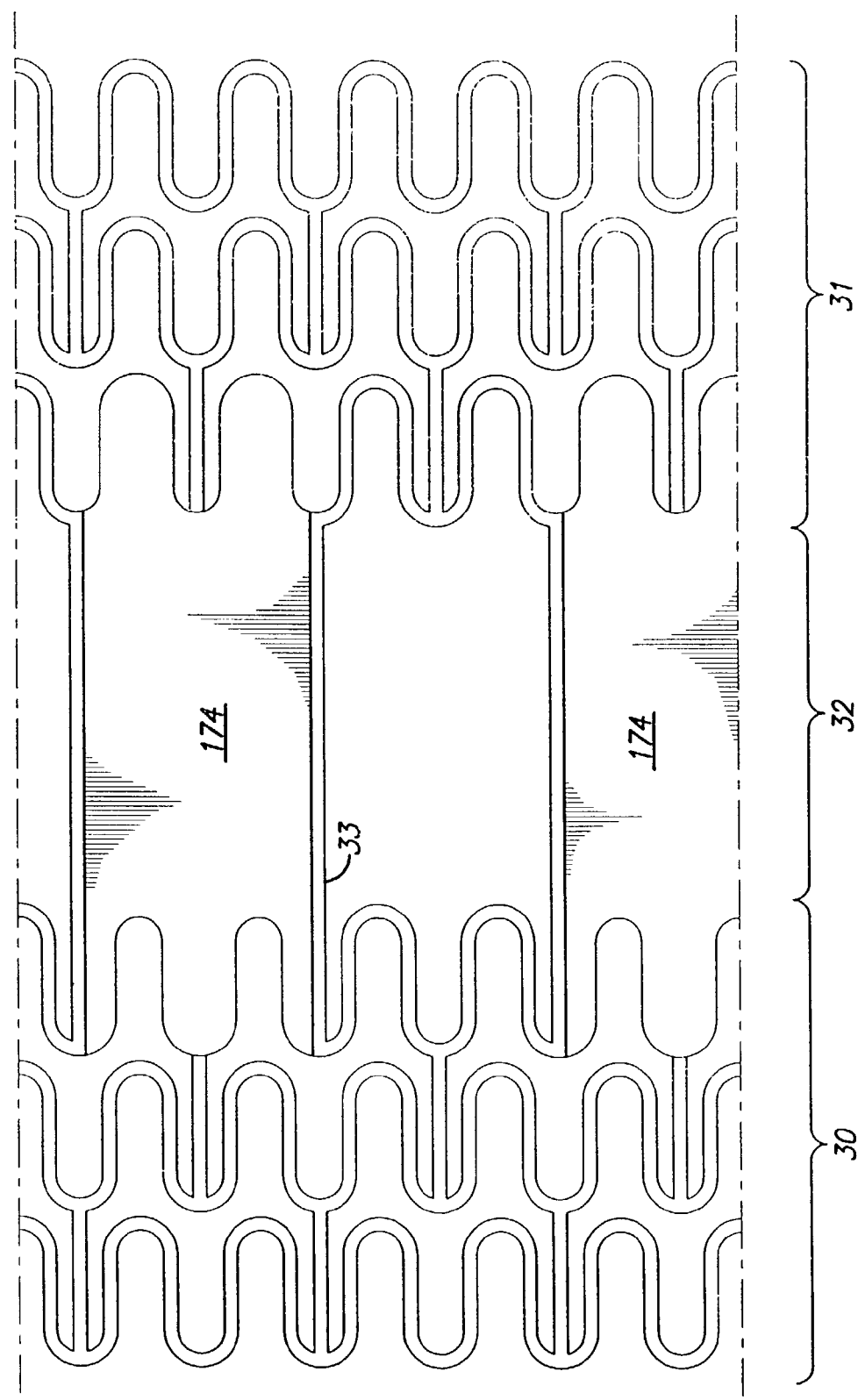
FIG. 13 is a plan view of a flattened stent depicting a covering over portions of the stent.

It may be desirable to provide a cover on one or more portions of the stent 10 of the present invention. As shown in FIG. 13, for example, the stent cover 174 covers portions of the central section which will come in contact with the fibrous cap. The stent cover is used to strengthen and support the area in the fibrous cap to prevent rupture. Since only a portion of the central section is covered, the remaining open sections will develop smooth muscle cell growth over the central section struts 33 thereby further supporting the area around the vulnerable plaque 27. Portions of the distal section and proximal section 30, 31 also can be covered with the stent cover 174. The stent cover can include materials such as PTFE or ePTFE, or their equivalent. The stent cover can be attached to the stent by various means including adhesives or laser bonding. Further, it is desirable that the stent cover have at least some elastic properties so that as the stent expands from a delivered diameter to an implanted diameter, the stent cover does not distort or prevent stent expansion.

Figure 14:
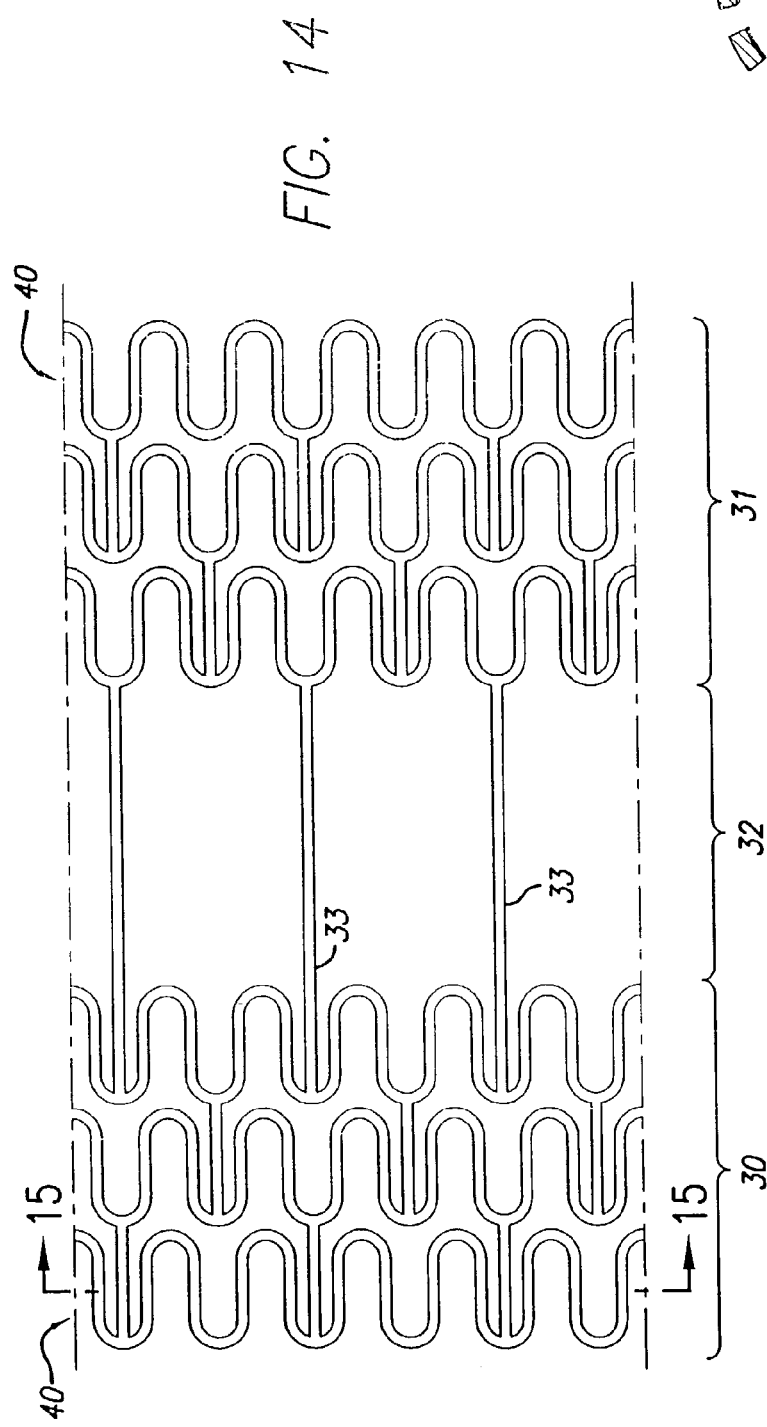
FIG. 14 is a plan view of a flattened stent having a drug coating on selected portions.
Figure 15:
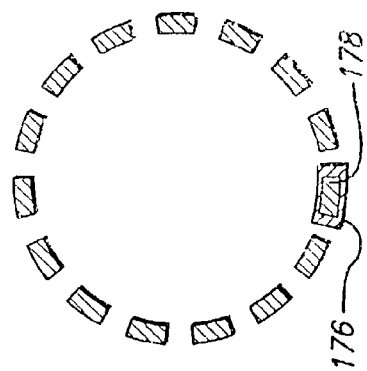
FIG. 15 is a cross-sectional view taken along lines 15-15 depicting the drug coating on a portion of the stent.

The stent 10 may also be used in connection with a therapeutic agent to perform a variety of functions, from preventing blood clots to promoting healing. As an example and as shown in FIGS. 14 and 15, an active agent coated 176 on struts 178 in the distal and/or proximal sections 30, 31 can inhibit the activity of endothelial cells. Similarly, an active agent coated on selective cylindrical rings 40 can also inhibit the activity of smooth muscle cells. More specifically, the active agent is aimed at inhibiting abnormal or inappropriate migration and proliferation of smooth muscle cells. Importantly, any use of a therapeutic agent on the stent distal and proximal sections 30, 31 to inhibit cell growth, must be balanced with the objective of the central section 32 to promote cell growth over the vulnerable plaque area 27.

The active agent 176 can also include any substance capable of exerting a therapeutic or prophylactic effect in the practice of the present invention. The agent can also be for enhancing wound healing in a vascular site or improving the structural and elastic properties of the vascular site. The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

One particularly useful therapeutic agent for coating the stent of the invention is everolimus (available from Norvatis Pharma AG) which is a drug in the same family as rapamycin. Other examples of therapeutic agents include rapamycin, actinomycin D (ActD), or derivatives and analogs thereof, or COSMEGEN. ActD is manufactured by Sigma-Aldrich, 1001 West Saint Paul Avenue, Milwaukee Wis. 53233. COSMEGEN is available from Merck. Synonyms of actinomycin D include dactinomycin, actinomycin IV, actinomycin 11, actinomycin X1, and actinomycin C1. Examples of agents include other antiproliferative substances as well as antineoplastic, anti-inflammatory, antiplatelet, anticoagulant, antifibrin, antithrombin, antimitotic, antibiotic, and antioxidant substances. Examples of antineoplastics include taxol (paclitaxel and docetaxel). Examples of antiplatelets, anticoagulants, antifibrins, and antithrombins include sodium heparin, low molecular weight heparin, hirudin, argatroban, forskolin, vapiprost, prostacyclin and pro stacyclin analogs, dextran, D-phe-pro-arg-chloromethylketone (synthetic antithrombin), dipyridamole, glycoprotein, 11b/111a platelet membrane receptor antagonist, recombinant hirudin, thrombin inhibitor (available from Biogen), and 7E-3B® (an antiplatelet drug from Centocore). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as Captopril (available from Squibb), Cilazapril (available from Hoffman-LaRoche), or Lisinopril (available from Merck); calcium channel blockers (such as Nifedipine), colchicine fibroblast growth factor (FGF) antagonists, fish oil (omega 3-fatty acid), histamine antagonist, Lovastatin (an inhibitor of HMG-CoA reductase, a cholesterol lowering drug from Merck), monoclonal antibodies (such as PDGF receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone.

The stent 10 of the present invention can be made in many ways. One method of making the stent is to cut a thin-walled tubular member, such as stainless steel tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as is well known in the art.

After laser cutting the stent pattern the stents are preferably electrochemically polished in an acidic aqueous solution such as a solution of ELECTRO-GLO#300, sold by ELECTRO-GLO Co., Inc. in Chicago, Ill., which is a mixture of sulfuric acid, carboxylic acids, phosphates, corrosion inhibitors and a biodegradable surface active agent. Other electropolishing solutions are well known in the art. The stents may be further treated if desired, for example by applying a biocompatible coating.

Other methods of forming the stent of the present invention can be used, such as chemical etching; electric discharge machining; laser cutting a flat sheet and rolling it into a cylinder; and the like, all of which are well known in the art at this time.

The stent of the present invention also can be made from metal alloys other than stainless steel, such as shape memory alloys. Shape memory alloys are well known and include, but are not limited to, nickel-titanium and nickel/titanium/ vanadium. Any of the shape memory alloys can be formed into a tube and laser cut in order to form the pattern of the stent of the present invention. As is well known, the shape memory alloys of the stent of the present invention can include the type known as thermoelastic martensitic transformation, or display stress-induced martensite. These types of alloys are well known in the art and need not be further described here.

Importantly, a stent formed of shape memory alloys, whether the thermoelastic or the stress-induced martensite-type, can be delivered using a balloon catheter of the type described herein, or in the case of stress induced martensite, be delivered via a catheter without a balloon or a sheath catheter.

While the invention has been illustrated and described herein, in terms of its use as an intravascular stent, it will be apparent to those skilled in the art that the stent can be used in other body lumens. Further, particular sizes and dimensions, number of peaks per ring, materials used, and the like have been described herein and are provided as examples only. Other modifications and improvements may be made without departing from the scope of the invention.

What is claimed:

1. An intravascular stent for use in a body lumen, comprising:
    a body, the body defining a single stent structure and including a distal section, a proximal section, and a central section positioned between the distal section and the proximal section, each section being aligned along a common longitudinal axis forming the stent;
    the distal section and the proximal section each having a plurality of cylindrical rings;
    the cylindrical rings of the distal section and the proximal section each including an undulating pattern of U-shaped portions forming peaks and valleys with straight portions parallel to the longitudinal axis of the stent and extending between the peaks and valleys, wherein the peaks of adjacent cylindrical rings are circumferentially aligned along the stent;
    a plurality of links interconnecting adjacent cylindrical rings; and
    a plurality of struts within the central section forming a connection between the distal section and the proximal section;
    wherein the central section is configured to have a density promoting smooth muscle cell growth and to have a longitudinal length at least as long as a longitudinal ring length of a ring of the distal section or the proximal section.

2. The stent of claim 1, wherein the link pattern is circumferentially offset between adjacent rings.

3. The stent of claim 1, wherein a distal end of each strut is circumferentially aligned with a proximal end of the strut.

4. The stent of claim 3, wherein the struts within the central section include straight struts.

5. The stent of claim 3, wherein at least one of the struts within the central section includes a first straight portion, an undulating member and a second straight portion, the undulating member being positioned between the first and second straight portions.

6. The stent of claim 3, wherein at least one of the struts within the central section includes a first straight arm, a series of undulating members and a second straight arm, the series of undulating members being positioned between the first and second straight arms.

7. The stent of claim 1, wherein the central section includes at least one pair of U-shaped portions.

8. An intravascular stent for use in a body lumen, comprising:
    a body, the body defining a single stent structure and including a distal section, a proximal section, and a central section positioned therebetween;
    the distal section and the proximal section each having a plurality of interconnected cylindrical rings, each cylindrical ring having a first delivery diameter and a second expanded diameter;
    each cylindrical ring having a proximal end and a distal end and a cylindrical wall extending circumferentially between the proximal end and the distal end of the cylindrical ring;
    at least one straight link attaching each cylindrical ring to an adjacent cylindrical ring, the links being positioned within the cylindrical wall of the cylindrical ring; and
    a plurality of struts within the central section positioned about the circumference of the central section, wherein the struts connect the distal section to the proximal section;
    wherein the central section is configured to have a density promoting smooth muscle cell growth and to have a longitudinal length at least as long as a longitudinal ring length of a ring of the distal section or the proximal section.

9. The stent of claim 8, wherein the links are parallel to the longitudinal axis of the strut.

10. The stent of claim 8, wherein the link pattern is circumferentially offset between adjacent rings.

11. The stent of claim 8, wherein a distal end of each strut is circumferentially aligned with a proximal end of the strut.

12. The stent of claim 11, wherein the struts within the central section include straight struts.

13. The stent of claim 11, wherein at least one of the struts within the central section includes a first straight portion, an undulating member and a second straight portion, the undulating member being positioned between the first and second straight portions.

14. The stent of claim 11, wherein at least one of the struts within the central section includes a first straight arm, a series of undulating members and a second straight arm, the series of undulating members being positioned between the first and second straight arms.

15. The stent of claim 8, wherein each of the cylindrical rings of the distal section and the proximal section include an undulating pattern of U-shaped portions forming peaks and valleys with straight portions parallel to the longitudinal axis of the stent extending between the peaks and valleys, wherein the peaks of adjacent cylindrical rings are circumferentially aligned along the stent.

16. The stent of claim 8, wherein the stent is formed from a tube.

17. The stent of claim 8, wherein the stent is formed from a metal alloy.

18. The stent of claim 8, wherein the stent is formed from stainless steel.

19. The stent of claim 8, wherein the stent is formed from a shape memory alloy.

20. The stent of claim 19, wherein the stent is formed from the group of shape memory alloys consisting of nickel-titanium and nickel/titanium/vanadium.

21. The stent of claim 8, wherein the stent is formed from a pseudoelastic metal alloy.

22. The stent of claim 21, wherein the stent is formed from the group of pseudoelastic metal alloys consisting of nickel-titanium and nickel/titanium/vanadium.

23. The stent of claim 8, wherein at least a portion of the distal section rings are coated with a therapeutic drug to reduce cell growth distal to vulnerable plaque existing in the body lumen.

24. The stent of claim 8, wherein at least a portion of the proximal section rings are coated with a therapeutic drug to reduce cell growth proximal to vulnerable plaque existing in the body lumen.

25. The stent of claim 8, wherein at least a portion of the distal section rings and the proximal section rings are coated with a therapeutic drug to reduce cell growth on either side of vulnerable plaque existing in the body lumen.

26. The stent of claim 8, wherein the central section includes at least one pair of U-shaped portions.

* * * * *